United States Patent
Gu et al.

(10) Patent No.: US 9,207,177 B2
(45) Date of Patent: Dec. 8, 2015

(54) OPTICAL SENSOR FOR BROMIDE ION

(71) Applicants: Jason Gu, Pittsburgh, PA (US); Peter C. Foller, San Francisco, CA (US); Jacob Melby, Pittsburgh, PA (US)

(72) Inventors: Jason Gu, Pittsburgh, PA (US); Peter C. Foller, San Francisco, CA (US); Jacob Melby, Pittsburgh, PA (US)

(73) Assignee: Sensevere, LLC, Pittsburgh, PA (US)

( * ) Notice: Subject to any disclaimer, the term of this patent is extended or adjusted under 35 U.S.C. 154(b) by 0 days.

(21) Appl. No.: 14/040,173

(22) Filed: Sep. 27, 2013

(65) Prior Publication Data

US 2014/0087476 A1    Mar. 27, 2014

Related U.S. Application Data

(60) Provisional application No. 61/706,378, filed on Sep. 27, 2012.

(51) Int. Cl.
| | | |
|---|---|---|
| *G01N 21/64* | (2006.01) | |
| *G01N 31/22* | (2006.01) | |
| *G01N 33/18* | (2006.01) | |
| *G01N 21/78* | (2006.01) | |
| *G01N 21/63* | (2006.01) | |
| *G01N 21/75* | (2006.01) | |

(52) U.S. Cl.
CPC .............. *G01N 21/643* (2013.01); *G01N 21/78* (2013.01); *G01N 31/22* (2013.01); *G01N 33/182* (2013.01); *G01N 21/64* (2013.01); *G01N 21/6428* (2013.01); *G01N 33/18* (2013.01); *Y10T 436/19* (2015.01); *Y10T 436/193333* (2015.01)

(58) Field of Classification Search
CPC . G01N 21/643; G01N 21/6428; G01N 21/64; G01N 21/63; G01N 21/62; G01N 21/00; G01N 21/78; G01N 21/77; G01N 21/75; G01N 31/22; G01N 31/00; G01N 33/182; G01N 33/18; G01N 33/00; Y10T 436/193333; Y10T 436/19; Y10T 436/00
USPC ........... 436/125, 124; 422/82.08, 82.05, 68.1, 422/50
See application file for complete search history.

(56) References Cited

FOREIGN PATENT DOCUMENTS

| EP | 0 634 646 A1 * | 7/1994 | .............. G01N 21/78 |
|---|---|---|---|
| WO | WO 2012/098346 A1 * | 7/2012 | .............. G01N 21/27 |

OTHER PUBLICATIONS

Selcuk, Huseyin et al., Behavior of bromide in the photoelectrocatalytic process and bromine generation using nanoporous titanium dioxide thin-film electrodes, Chemosphere, 2004, 54, 969-974.*
International Search Report for PCT/US2013/062354, Jan. 7, 2014; obtained on Dec. 16, 2014, pp. 1-5.*

* cited by examiner

*Primary Examiner* — Christine T Mui
(74) *Attorney, Agent, or Firm* — Cohen & Grigsby, P.C.

(57) ABSTRACT

Methods and systems to determine a concentration of bromide ions in an aqueous sample are disclosed. The method involves the oxidation of bromide ions to bromine, followed by bromination of a colored or fluorescent reporter compound which may be detected by spectrophotometric means. The relative change in color or fluorescence upon bromine binding to the reporter compound may then be used to determine a quantitative concentration of bromide ions in the sample. The system utilizes a photocatalytic coating in a sample chamber, a source of reporter compound in fluid communication with the sample chamber, light sources that may activate the photocatalyst and excite the reporter compound, an optical detection unit capable of receiving a light signal from the second light source after it has passed through the sample chamber, and various pumps, valves or injection syringes that regulate the flow of sample and reporter compound into and out of the sample chamber.

21 Claims, 8 Drawing Sheets

OPTICAL SENSOR FOR BROMIDE ION

CROSS-REFERENCE TO RELATED APPLICATIONS

This application claims the benefit of U.S. Provisional Application No. 61/706,378, filed Sep. 27, 2012, the contents of which are hereby incorporated by reference in its entirety.

BACKGROUND

1. Technical Field of the Invention

This invention pertains generally to methods and systems for the determination of an ion concentration in a liquid sample. More specifically, the invention pertains to a method and system for the determination of bromide ion concentrations in aqueous samples.

2. Description of the Related Art

While bromides are generally considered to be non-toxic salt compounds, bromide contamination of water is of great concern due to the resultant brominated organics, specifically brominated trihalomethanes, which form during chlorination of drinking water. Studies have shown a link between ingestion of brominated trihalomethanes and several types of cancer and birth defects.

Bromide is most often found in nature in the form of salts with sodium, potassium, and other ions, and occurs in varying amounts in ground and surface waters. For example, bromide concentrations in seawater are generally in the range of 65 mg/l to well over 80 mg/l, while concentrations in fresh water typically range from trace amounts to about 0.5 mg/l (*Bromide in the Natural Environment: Occurrence and Toxicity*, M. Flury & A. Papritz, Journal of Environmental Quality 22(4):747-758, October-December 1993; *Bromide in Drinking water*, Background document for development of WHO Guidelines for Drinking-water Quality, World Health Organization 2009). Fresh water sources located near coastal regions may have much higher concentrations as a result of seawater intrusion and sea-spray effected precipitation. Further, the bromide content of ground waters and stream baseflows may also be affected by connate water (e.g., water trapped in geological formations).

One additional source of elevated bromide levels in freshwater supplies is the hydraulic fracturing of Marcellus shale formations used in the production of natural gas. While most geological formations have little bromide, limestone and shale are rich in this ion. After hydraulic fracture is complete, the internal pressure of the geologic formation causes water injected during fracture to rise to the surface where it is generally recovered and stored in tanks or pits prior to disposal or recycling. This recovered water, commonly referred to as produced water or flow-back water, carries with it numerous chemicals added during the hydraulic fracturing process in addition to salts (chlorides, bromides, and sulfides of calcium, magnesium, and sodium), metals (barium, manganese, iron, and strontium, among others), bacteria and hydrocarbons leached from the geologic formation. As such, typical flow-back water may contain contamination levels of salts, metals and dissolved solids (total organic and inorganic dissolved solids) that are as much as several thousand fold over the EPA's maximum allowable level.

TABLE 1

| | Flowback Water Chemistry (mg/L) | EPA's Maximum Contaminant Level (mg/L) | Multiples of Contamination |
|---|---|---|---|
| Bromide | 445 | 0.00005 as ethylene bromide<br>0.01 as bromate<br>0.08 as total trihalomethanes | >30,000 |
| Chloride | 41,850 | 250 | 167 |
| TDS* | 67,300 | 500 | 135 |
| Hardness | Up to 55,000 | — | Extremely hard |

*Total Dissolved Solids

One clear example of bromide contamination was found in the Monongahela River in western Pennsylvania. A study conducted by Carnegie Mellon University found that bromide levels rose in 2010 and have remained elevated. Whether this is due to direct discharge of flow-back water into the river, or contamination of local tributaries due to poor or improper handling is not clear. Consequently, communities in close proximity to such operations are greatly concerned over whether or not the water recycling to and from surface containment tanks is carried out correctly. Table 1 shows analytical data on hydraulic fracture flow-back water sampled from the Marcellus Shale geological area (*Sampling and Analysis of Water Streams Associated with the Development of Marcellus Shale Gas*, Prepared for "Marcellus Shale Coalition" by Thomas Hayes, Dec. 31, 2009). Of significance is that the bromide ion was found at average concentrations of 445 mg/L, approximately 30,000 times greater than that of normal surface water. Improper handling of such water would easily lead to contamination of freshwater sources.

Table 1 also shows the extremely high hardness levels of the flow-back water, which are indicative of high concentrations of total dissolved salts, such as bromide, chloride, magnesium and manganese. While low levels of certain of these salts in aquifers are crucial for the growth and development of wildlife and fish in the Marcellus geologic area, high concentrations can be extremely deleterious. For example, there are eleven public water treatment intakes on the Monongahela River, supplying approximately 350,000 customers. The bromide contamination recently found in this water source may react with the disinfectants used at these eleven public water treatment plants to form brominated trihalomethanes. The greater the contaminations level in the river water, the more brominated trihalomethanes in the treated water, and studies have shown a link between ingestion of trihalomethanes and several types of cancer and birth defects.

A simple and low cost, fast response sensor for bromide ion would be desirable for identifying contamination of ground and surface waters. Ideally, a sensor would be capable of establishing a concentration gradient leading from dilute concentrations as low as single digit parts-per-billion up to the sources of contamination at hundreds of mg/L. Thus, such a sensor would require sensitivity to levels of bromide ion spanning several orders of magnitude.

Other potential applications of such a method and sensor include monitoring of bromide ion in solution mined sodium chloride brine, as is used as feedstock in the chlor-alkali process to produce chlorine and sodium hydroxide (caustic soda). Bromide in brine would become a bromine contaminant in chlorine, which is of concern in many of chlorine's downstream uses.

Bromide concentrations have historically been determined spectrophotometrically by the bromination of a chemical dye after oxidation of bromide. Prior art methods for the determination of bromide concentrations have used high heats, strong acids, and compounds such as carbon tetrachloride or concentrated hydrogen peroxide, all of which pose ecological and health hazards. Further, the processes have involved distillation, extensive separations, and/or centrifugation steps. As such, none have been amenable to rapid detection of bromide ion concentrations. And none have been portable so that they may be used in the field.

Thus, what is needed is a rapid and low cost method and system for the detection of bromide ion over a broad concentration range.

SUMMARY

The presently disclosed invention provides such a method and system for rapid and low cost detection of bromide ions in a liquid sample. Further, the method and system may detect concentrations of the bromide ion ranging from single digit parts-per-billion to hundreds of mg/L.

According to its major aspects, and briefly stated, the present invention includes a dual chamber system for detection of bromide ions in an aqueous sample. The dual chamber system comprises a reaction chamber having a fluid inlet, a fluid outlet, and an inner surface, the reaction chamber containing a photocatalyst, wherein a fluid sample enters the reaction chamber through the fluid inlet; a source of reporter compound in fluid communication with the fluid outlet of the reaction chamber; a detection chamber having a fluid inlet and a fluid outlet, wherein the detection chamber is configured to receive the fluid sample from the fluid outlet of the reaction chamber; a first light source configured to illuminate at least a portion of the reaction chamber; a second light source configured to illuminate at least a portion of the detection chamber; and an optical detection unit capable of receiving a light signal from the second light source after it has passed through the detection chamber.

Embodiments of the dual chamber system may further comprise a waste disposal container in fluid communication with the fluid outlet of the detection chamber; and a probe attachable to the fluid inlet of the reaction chamber, wherein the aqueous sample flows into and through the probe into the fluid inlet of the reaction chamber. Yet further embodiments of the dual chamber system may additionally comprise a wavelength filter placed in front of the optical detection unit, wherein the wavelength filter limits the signal from the second light source to light corresponding to the characteristic emission of the reporter compound. Still further embodiments of the dual chamber system may additionally comprise an injection valve at the fluid inlet of the reaction chamber; a valve at the fluid outlet of the reporter compound source; a valve at the fluid outlet of the detection chamber; a pump configured to move the aqueous sample from the fluid inlet of the reaction chamber to a fluid outlet of the detection chamber; a programmable flow controller to limit the rate of fluid transport; and programmable electronic computing means for controlling the sequencing of the valves and the pump.

In embodiments of the dual chamber system, at least a portion of the reaction chamber is capable of passing a light signal from the first light source, and at least a portion of the detection chamber is capable of passing a light signal from the second light source. The first and second light sources may be LEDs, and the optical detection unit may be a photodiode, a photodiode array, a charge coupled device, or a photomultiplier tube. Further, the photocatalyst may be provided as a coating on the inner surface of the reaction chamber, or as a coating on beads contained within the reaction chamber. The reporter compound may be a chemical dye selected from the group comprising fluorescein, phenol red, methyl orange, brom cresol purple, phenosafranin, rosaniline, and N,N-Diethyl-p-Phenylenediamine Oxalate.

Embodiments of the present invention are also directed to a single chamber system for detection of bromide ions in an aqueous sample. The single chamber system comprises a sample chamber having a fluid inlet, a fluid outlet, and an inner surface, the sample chamber containing a photocatalyst, wherein the aqueous sample enters the sample chamber through the fluid inlet; a source of reporter compound in fluid communication with the sample chamber; a first light source configured to illuminate at least a portion of the sample chamber with light of a first wavelength; a second light source configured to illuminate at least a portion of the sample chamber with light of a second wavelength; and an optical detection unit capable of receiving a light signal from the second light source after it has passed through the sample chamber.

Embodiments of the single chamber system may further comprise an injection syringe and motor configured to inject a buffer solution to the aqueous sample in the sample chamber, a second injection pump and motor configured to inject the reporter compound into the sample chamber, and a means for mixing the sample in the sample chamber Further, the single chamber system may additionally comprise programmable electronic computing means for controlling the sequencing of the injection syringes and the valve.

Embodiments of the present invention are also directed to a method for detection of bromide ions in an aqueous sample. The method comprises providing a volume of aqueous sample; admixing the volume of aqueous sample with a photocatalyst; exposing the volume of aqueous sample admixed with the photocatalyst to a source of light, wherein the light causes the photocatalyst to produce free hydroxyl radicals which react with bromide ions to produce bromine; and admixing a reporter compound with the volume of aqueous sample, wherein the bromine reacts with the reporter compound to change the color or fluorescence emission of the reporter compound.

BRIEF DESCRIPTION OF THE DRAWINGS

Aspects, features, benefits and advantages of the embodiments herein will be apparent with regard to the following description, appended claims, and accompanying drawings, wherein:

DETAILED DESCRIPTION

Figure 1:
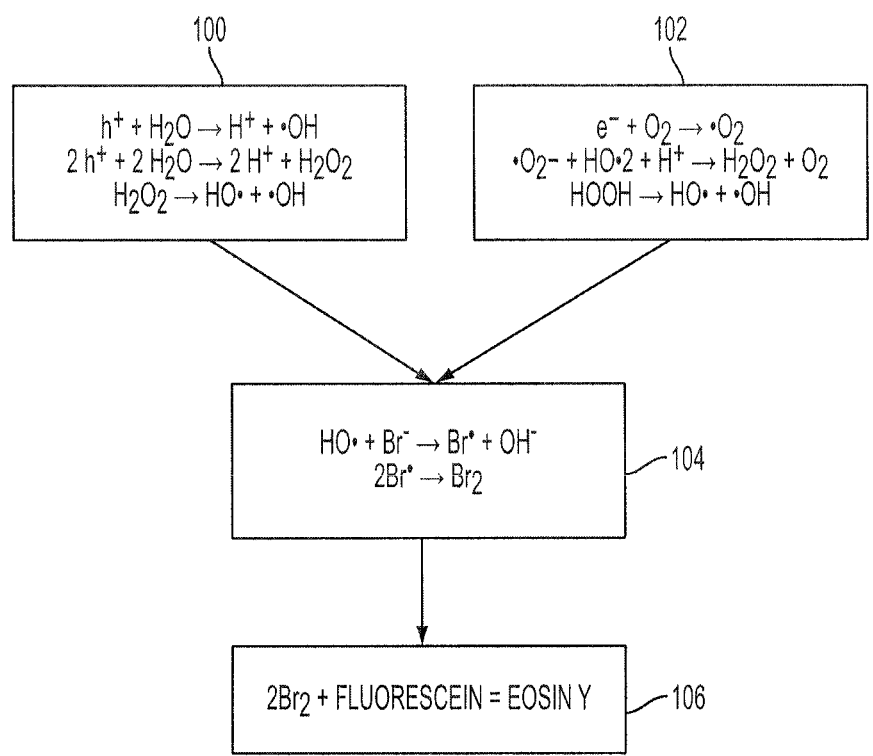
FIG. 1 depicts an exemplary flow diagram of a process for the detection of bromide ions in a sample in accordance with certain embodiments of the present invention.

In the following description, the present invention is set forth in the context of various alternative embodiments and implementations involving a method and system useful for the determination of bromide ion concentrations in a water sample such as, for example, a ground water sample. Briefly stated, the method involves the oxidation of bromide ions to bromine, followed by bromination of a colored or fluorescent target compound, which may be detected by spectrophotometric means. The relative change in color or fluorescence emission upon bromine binding to the target compound may then be used to determine a quantitative concentration of bromide ions in the sample.

The conversion of bromide to bromine may be carried out using methods known in the art. For example, bromide ions may be oxidatively converted to elemental bromine using chemical oxidizing agents such as, for example, chloramine T or the eerie ion (e.g., eerie ammonium nitrate, ceric ammonium sulfate, etc.). Alternatively, bromide ions may be oxidized to elemental bromine using photoassisted means. For example, in the presence of light a photocatalyst may generate hydroxyl radicals from the oxidation of water or reduction of dissolved oxygen in an aqueous solution. These hydroxyl radicals may then oxidize the bromide ions to elemental bromine.

There is a great amount of literature on photoassisted (i.e. photocatalytic) oxidations with Titanium dioxide, $TiO_2$. It has been theorized that absorption of a photon by Titanium dioxide produces an electron-hole pair. The photogenerated holes oxidize directly contacting organic compounds. The electrons then reduce oxygen to surface-bound peroxide, that also photooxidizes organic compounds. Titanium dioxide, particularly in the anatase form, is a photocatalyst under ultraviolet (UV) light. Recently it has been found that titanium dioxide, when spiked with nitrogen ions or doped with metal oxide like tungsten trioxide, is also a photocatalyst under either visible or UV light. It should be appreciated that any proposed theory presented herein is for illustrative purposes only, and the claims and disclosure should not be construed as being bound thereto. Furthermore, any photocatalyst capable of generating hydroxyl radicals in a aqueous solution is envisioned within the scope of the present invention. For example, Certain other exemplary photocatalysts may require different light wavelengths for activation. For example, titanium oxynitride (TiN), titanium-aluminum nitride (TiAlN), $SrTiO_3$, and $K_4NbO_{17}$ may be used as photocatalysts in the present invention.

While bromine has an absorption that may be optically detected, its extinction coefficient of 170 $mol^{-1}cm^{-1}$ is rather low. Thus, at low concentrations of bromine, it is more useful to detect the action of the bromine on a dye either having a very high extinction coefficient or an intense fluorescence in response to UV activation. As such, the bromine thus formed may then be reacted with a reporter compound that is capable of a color or fluorescence emission change upon bromination. Exemplary reporter compounds are chemical dyes such as, for example, phenol red, fluorescein, methyl orange, brom cresol purple, phenosafranin, rosaniline, and N,N-Diethyl-p-Phenylenediamine Oxalate.

Referring now to the drawings, an exemplary flow diagram of a process for the detection of bromide ions according to an embodiment of the present invention is shown in FIG. 1. A photocatalyst may be used to decompose water to produce hydroxyl radicals (.OH, Std. Potential=+3.06 V), which are thermodynamically capable of oxidizing bromide ion ($Br^-$) to bromine (Br*, Std. Potential=+1.07 V). The oxidative and reductive photocatalytic reactions for water are represented at steps 102 and 104, respectively. That is, step 102 shows the oxidation of water by a photocatalyst, while step 104 shows the reduction of dissolved oxygen, typically at 5-10 mg/L in water, by a photocatalyst.

Figure 2:
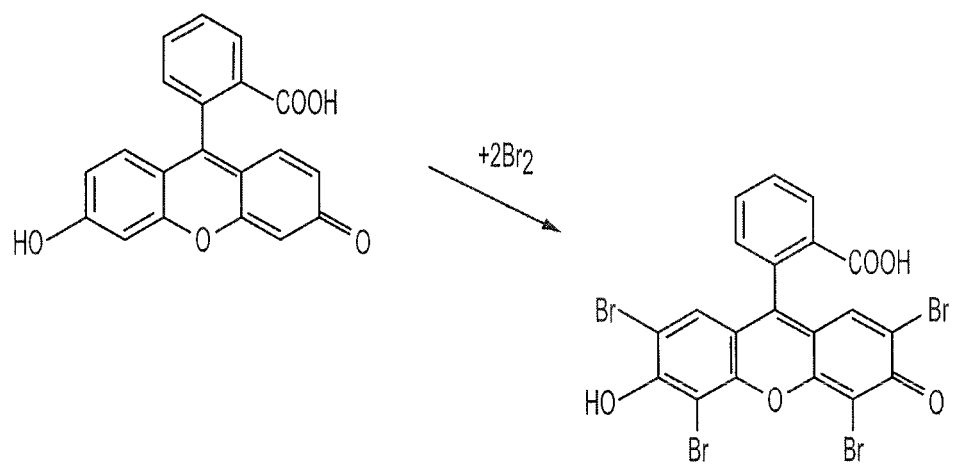
FIG. 2 illustrates the bromination reaction of fluorescein to produce Eosin Y.

Step 106 illustrates the oxidation of bromide to bromine by the hydroxyl radicals formed at steps 102 and/or 104. Step 108 illustrates the reaction of fluorescein with bromine to form a second dye Eosin Y. This specific chemical reaction is also shown in FIG. 2, wherein bromination of the fluorescent dye fluorescein (2-(6-hydroxy-3-oxoxanthen-9-yl)benzoate) leads to the tetrabomo-derivative named Eosin Y (2-(2,4,5,7-tetrabromo-3-oxido-6-oxoxanthen-9-yl)benzoate).

Figure 3:
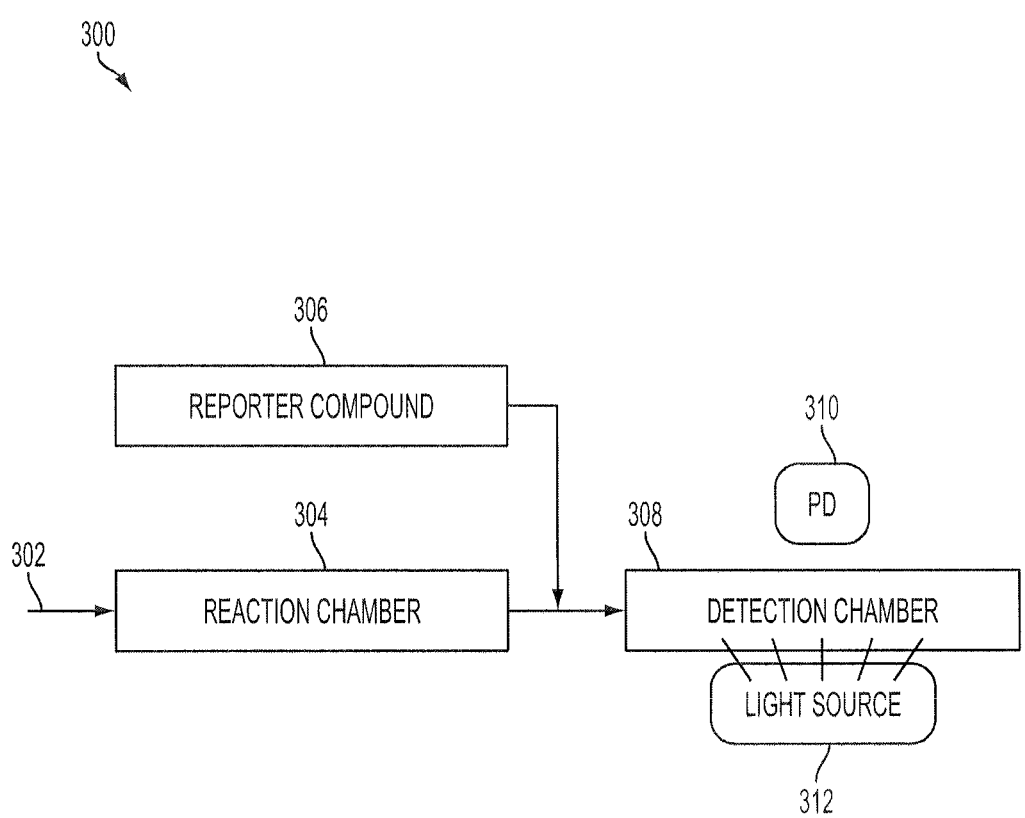
FIG. 3 illustrates a schematic diagram of a system for the detection of bromide ion in accordance with certain embodiments of the present invention.

The general layout of a two chamber system for the detection of bromide ion in accordance with certain embodiments of the present invention is shown in FIG. 3, generally designated by reference number 300. As shown, the system 300 may comprise of a reaction chamber 304, in which the bromide ion is reacted to form bromine. The mechanism of reaction can range from addition of an oxidizing species to photocatalytic oxidation using a catalyst and light source. The water with the newly produced bromine is reacted with a reporter compound provided from a source 306. The resultant mixture may then enter the detection chamber 308.

As shown in FIG. 3, the detection chamber 308 may use a light source 312 to cause characteristic emission from the reporter compound, which may be detected by a photodiode 310. A wavelength filter may be used to limit the signal to light corresponding to the characteristic emission of the reporter compound. In the specific embodiment discussed in FIG. 1, for example, the reporter compound was the chemical dye fluorescein. Alternatively, the detection chamber 308 may measure the absorbance of the reporter compound, in which case the light source 312 may not be required.

The oxidizing agent may be contained within a second chamber (not shown) in a concentrated form. This chamber may be configured to deliver the oxidant directly to the reaction chamber 304 after an aqueous sample has become contained therein. In alternate embodiments, a photocatalyst may be included in the reaction chamber 304 as a coating on an inner surface of the chamber, or on beads included within the chamber. In the instance where the oxidizing agent is a photocatalyst, the reaction chamber 304 may be a UV-transparent chamber, possibly as simple as a quartz tube.

Thus, in certain embodiments of the system 300, a photocatalyst coating such as, for example, an anatase $TiO_2$ coating may be applied to the inner surface of the reaction chamber 304. The geometry of the photocatalyst coating is arbitrary. In embodiments using an anatase $TiO_2$ coating, UV light, specifically UV light at a wavelength of about 365 nm, may be used to activate the $TiO_2$. Certain other exemplary photocatalysts may require different light wavelengths for activation. For example, titanium oxynitride (TiN), titanium-aluminum nitride (TiAlN), $SrTiO_3$, and $K_4NbO_{17}$ may necessitate the use of different wavelengths of light.

In certain other embodiments of the system 300, a photocatalyst coating may be applied to beads contained within the reaction chamber 304. That is, a bead having an exterior surface that is at least partially coated with a material that under illumination and in the presence of air is capable of assisting in (i.e. accelerating) the oxidation of organic compounds. The term "bead" is used broadly herein to mean a piece of material having virtually any three-dimensional shape (e.g. spherical, octahedral, prismatic, or of irregular cross-section).

In embodiments, the coating material may comprise $TiO_2$ particles having diameter on the order of 30-200 nm. $TiO_2$ (rutile) or $TiO_2$ (anatase) are particularly preferred for use in this invention, as they are widely known as photocatalysts in the oxidation of contacting organic compounds. Both are substantially nontoxic and environmentally harmless. Both are n-type semiconductors with 3 eV and 3.3 eV band gaps, respectively.

The aqueous sample may be sampled from a source 302 using any means known in the art. For example, a probe or tube may be submersed in the aqueous solution to be analyzed. A sample may then flow from the probe and enter the reaction chamber 304. Alternatively, a sample may be manually placed in the reaction chamber 304. Within the reaction chamber 304, the bromide ion may be oxidized to bromine using the methods described above.

Figure 4:
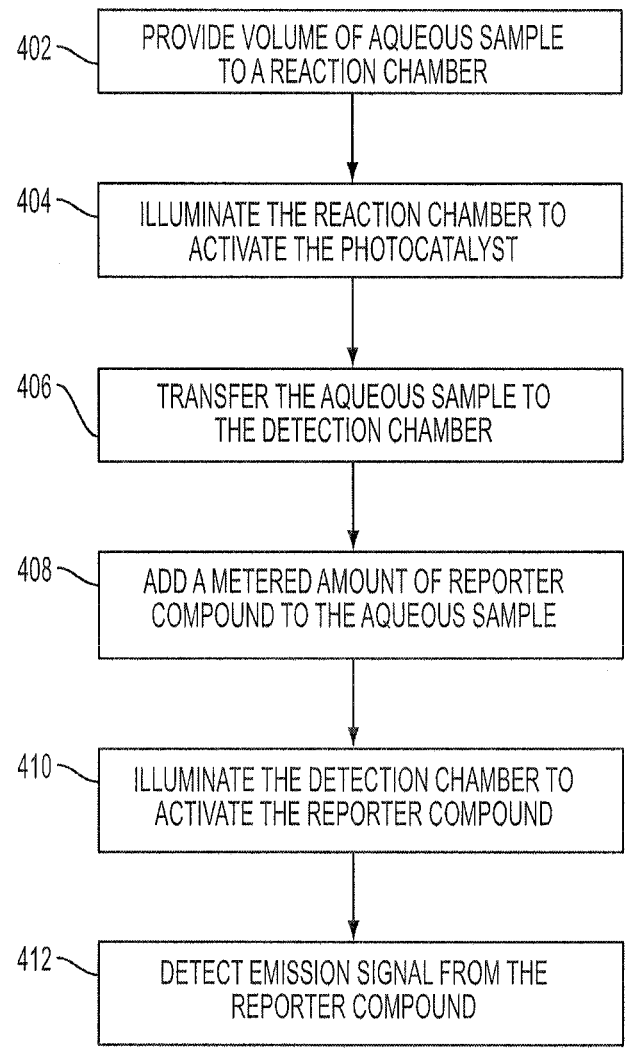
FIG. 4 illustrates an exemplary flow diagram of a process for the detection of bromide ions in a sample in accordance with certain embodiments of the present invention.

An exemplary embodiment of a method of use of the system is illustrated in FIG. 4. First, at 402, an aqueous sample which may contain bromide ions is introduced into the reaction chamber. In certain embodiments, this reaction chamber may be a flow-through UV-transparent chamber such as a quartz tube. In alternate embodiments, the reaction chamber may be a plastic vessel, such as a chamber, tube, or cuvette, which has a quartz or UV quality window. The reaction chamber may contain a commercial anatase $TiO_2$ photocatalyst coating on an inner surface or on glass micro beads. Hydroxyl radicals may be produced in the reaction chamber via illumination of the photocatalyst with a 365 nm (commodity) UV diode, as shown at 404. Illumination over a suitable length of time may then produce hydroxyl radicals in an amount sufficient to react with bromide ion to form bromine. The aqueous sample may then be transferred to a detection chamber, as shown at 406. This transfer may be accomplished by simple gravity, or by the action of air pressure or vacuum produced by a pump. In certain embodiments, the detection chamber may be a flow-through UV transparent optical cuvette.

At 408, a metered amount of reporter compound, such as fluorescein dye, may be added to the aqueous sample. This may happen at any point after exit from the reaction chamber. That is, the reporter compound may be added to the aqueous sample in the flow path just after exit from the reaction chamber but before entry to the detection chamber. Alternatively, the reporter compound may be added directly to the detection chamber after the aqueous sample has entered the chamber. The reporter compound may be mixed with the aqueous sample by action of entry to the flow path, or by the action of a mixing device. Any mixing device for liquids known in the art is envisioned as suitable for the system of the present invention. Suitable examples include paddle mixers, spray mixers, inline junctions (Y junctions, T junctions, 3 way intersections), designs where the interfacial area between the two fluids is maximized, twisting channels to force the two fluids to mix, and features on the walls like notches or groves.

At 408, exposure between the aqueous sample and the reporter compound over a sufficient length of time may generate a bromo-derivative of the reporter compound. For example, in a preferred embodiment, the reporter compound is fluorescein, which becomes tetrabrominated to form the dye Eosin Y (as shown in FIG. 2). At 410, a light source may be used to excite the reporter compound. As example, in embodiments using fluorescein as the reporter compound, the light source may be a UV light source that may activate the unreacted remainder of the fluorescein dye. At 412, excitation is suspended and the resultant fluorescence emission produced may be detected with an optical filter and photodiode. The optical filter is selected for the specific wavelengths within which the peaks of interest reside.

Pumps and valves may be included at various points along the flow path of the system to enable control of fluid movement. That is, valves may be included in the fluid inlet and fluid outlet of the reaction chamber, the fluid outlet of the reporter compound reservoir, and the fluid inlet and fluid outlet of the detection chamber. Such valves may be used to control the movement of the aqueous sample between chambers, to allow for specific metered amounts of fluids to be delivered to the reaction and detection chambers (e.g. the aqueous sample and the reporter compound), and to control the reactions times of the aqueous sample in the various portions of the system flow path. Exemplary valves include at least injection valves, switching valves, ball valves, check valves, slide valves and pinch valves. Pumps may be included to push or pull sample through the flow path of the system.

In certain embodiments, a single chamber may be used to react the bromide ions with an oxidizing agent and to generate element bromine. Thereafter, and within the same chamber, the elemental bromine may be reacted with a reporter molecule to generate a signal indicative of the concentration of bromide ions in the aqueous sample. As such, 406 in FIG. 4 may not be required. Rather, a volume of aqueous sample may be pulled into the single sample chamber, as indicated at 402. Such may be accomplished manually, or through the use of automated means such as, for example, by suction generated by a pump. In certain embodiments, this sample chamber may be a flow-through UV-transparent chamber such as a quartz tube. In alternate embodiments, the reaction chamber may be a plastic vessel, such as a chamber, tube, or cuvette, which has at least one quartz or UV quality window. That is, at least a portion of the chamber may have a region through which light in the wavelength range of 300 to 800 nm may pass relatively unobstructed. The reaction chamber may contain a commercial anatase $TiO_2$ photocatalyst coating on an inner surface or on glass micro beads.

The sample may be illuminated by light from a first light source, such as an LED, as indicated at 404, to encourage generation of an oxidizing species by the photocatalyst, such as hydroxyl radicals. As discussed above, a specific time period may be required to generate enough hydroxyl radicals to oxidize the full content of bromide ions. This time may be dependent on at least the concentration of bromide ions, the concentration of the photocatalyst, and the size of the sample chamber. A metered amount of the reporter compound may be added to the sample chamber, as indicated at 408 for the dual chamber system, which may be allowed to react with the elemental bromine for a specific time period. Here again, the time period may be dependent on at least the concentration of bromine, the concentration of the reporter compound, and the size of the sample chamber. Illumination and detection, as shown at 410 and 412, may be carried out as described above.

Figure 5:
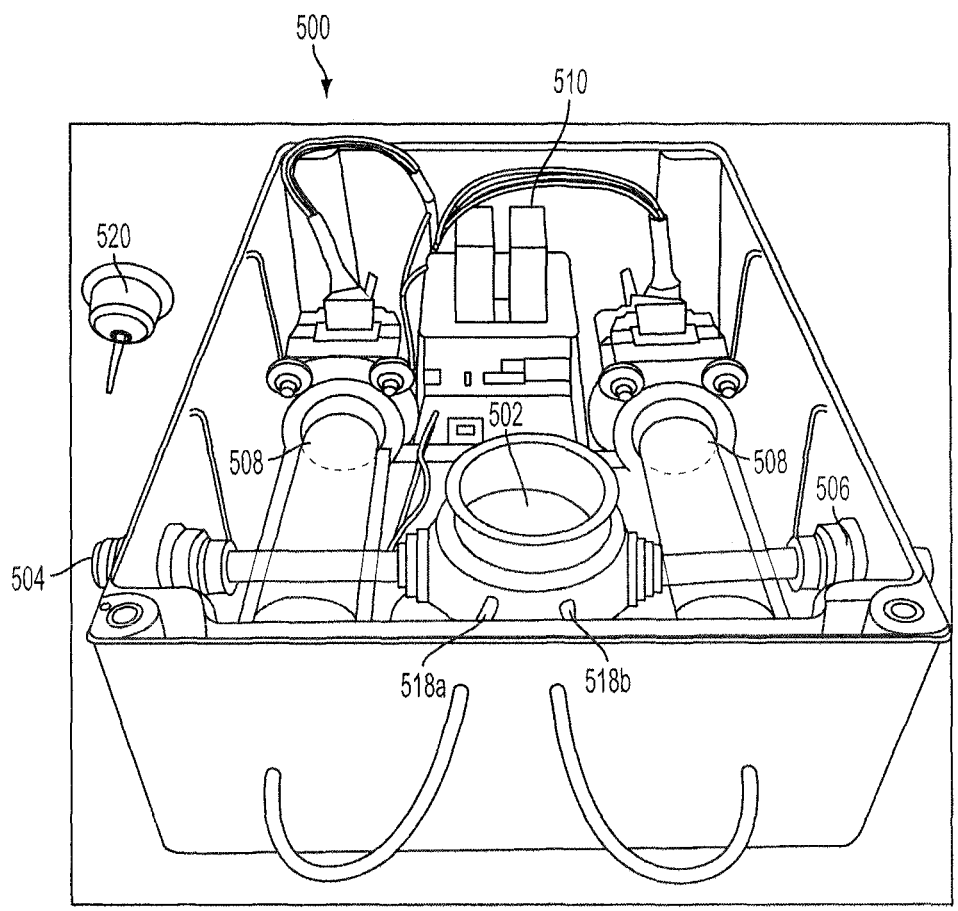
FIG. 5 illustrates a top view of a single chamber system for the detection of bromide ion in accordance with certain embodiments of the present invention.

An exemplary single chamber system is shown in FIG. 5, generally designated by reference number 500. As viewed from the top, the single chamber system 500 may comprise a sample chamber 502 having a fluid inlet 504 and fluid outlet 506 and fluid injection pumps and motors 508a and 508b and a sample pump. A first fluid injection pump and motor 508a may be configured to inject a buffer solution to the aqueous sample in the sample chamber 502 through an inlet port 518a.

A second injection pump and motor 508b may be configured to inject the reporter compound into the sample chamber 502 through inlet port 518b.

The system 500 may also comprise a pump (not shown) which may pull sample from the fluid inlet 504 into the sample chamber 502. In certain embodiments, the sample chamber 502 may be a pressure differential chamber. As such, activation of the pump to pull an aqueous sample into the sample chamber 502 will cause any prior fluid in the chamber to be expelled through the fluid outlet 506. Operation of the system 500 may be controlled by a controller 510 or any other programmable electronic computing means 510 known in the art. The controller 510 may controlling the sequencing of the injection syringes 508a and 508b, the pump, the first and second light sources, and the optical detection unit. That is, the system 500 may use a controller 510 which may have computational code that allows it to regulate and automate the timing of each of the aforementioned components in order to automate the measurement and detection of bromide ions in an aqueous sample. As such, a single button may be pushed to activate the system and acquire a bromide ion concentration reading In certain other embodiments of the systems of the present invention, a volume of aqueous sample may be pulled into a sample chamber, such as the single sample chamber 502 of FIG. 5, as also indicated at 402 in FIG. 4. The first injection syringe and motor 508a may be activated to add a buffer which may bring the pH of the aqueous sample in the sample chamber to within a certain predetermined optimal range. Continuous stirring may be provided by the mixer 520. This range may be dependent on the reporter compound chosen. For example, in embodiments using the reporter compound fluorescein, the optimal pH range may be between about 6.0 and 7.5. The amount of buffer added may depend on the specific of the aqueous sample (source) and the concentration of the buffer in the injection syringe. In certain embodiments, a pH probe may be incorporated into the sample chamber to measure the pH of the sample. The controller 510 may inject buffer from the first injection syringe 508 until a specific optimal pH is measured by the integrated pH probe.

The controller 510 may direct the second injection syringe and motor 508b to inject a reporter compound into the sample chamber 502. Here again, the mixer 520 may provide continuous mixing. The controller 510 may direct the first light source to illuminate at least a portion of the sample chamber, and thus activate the photocatalyst. After a specific length of time, the controller 510 may direct the second light source to illuminate at least a portion of the sample chamber to excite the reporter compound. A optical detection unit may then collect signal from the emission of the fluorescent sample.

In any of the embodiments of the systems discussed above, the chambers may be rinsed or washed between sample measurements. Such may be accomplished using water or additional sample. For example, in the system discussed with reference to FIG. 5, an automated wash cycle may be activated at the end of a reading cycle, during which sample is pulled through the sample chamber but no additional chemical agents are added, and no light sources are activated to initiate the photocatalyst.

The total amount of signal generated by any of the embodiments of the various systems of the present invention may be integrated over a specific time and across a specific wavelength region. This integrated signal may be used to determine a total concentration of bromide ions in the aqueous sample. Such may be done by reference to a known standard curve. That is, the signal generated by specific known amounts of bromide ion may be used to produce a calibration or standard curve which may allow the signal from single sample measurements to be numerically converted to mg/L or g/L quantities of bromide ion in the sample. Such is known in the art and is standard practice for one of skill in the art.

In the above description of a method of use of a system, the reporter compound described is a fluorescent chemical dye. As such, the optical measurements in the detection chamber would benefit from the use of a flow-through quartz cuvette or a plastic detection chamber with quartz windows. The cuvette or detection chamber may have any path length known and available in the art such as, for example, 1 cm. Further, the cuvette or detection chamber may be calibrated to achieve optimal signal. The bromine formed in the reaction chamber may be easily reacted under ambient conditions with a carefully metered feed from a reservoir of dilute reporter dye such as, for example, fluorescein dye (which is green) to form the brominated dye. In the case of fluorescein, tetrabromination produces the dye known as Eosin Y (which is a red). Thus, while the present method and system have been described in the context of detecting a fluorescent signal through specific excitation and emission detection, simple absorbance may be used to measure the conversion of the reported compound to its bromo-derivative.

In the case of a quasi-static combined reaction/detection chamber configuration, care needs to be taken of the configuration of the quartz window. Illumination for reaction and detection occurs within the same chamber; sufficient time is required between the reaction and detection light exposure. Given proper selection of the optical filter, the illumination for reaction and detection can occur simultaneously through two separate windows. However, it is necessary to darken the reaction illumination window to reduce cross-talk in the photodetector.

EXAMPLES

Figure 6:
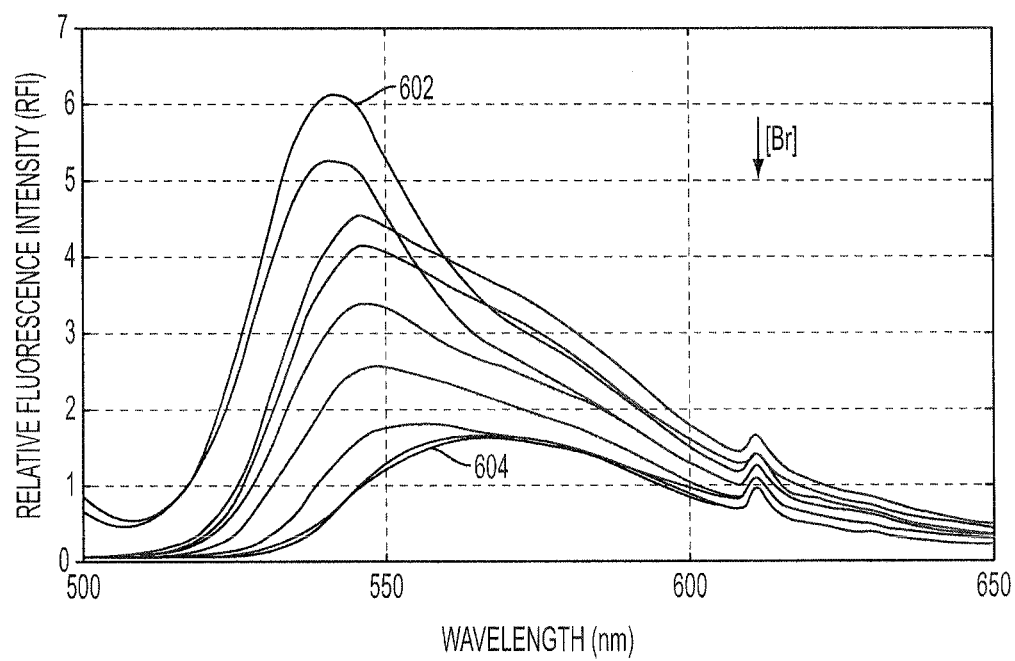
FIG. 6 shows a bromine-binding titration curve using fluorescein dye in reaction schemes according to certain embodiments of the present invention.

The method of the present invention was used to generate a standard curve which shows linearity over a broad range of bromide ion concentration. FIG. 6 shows results of the method from 0 to 1,000 mg/L of bromide ion taken over a 1 cm path length using a laboratory UV/vis spectrophotometer (Ocean Optics OL-770). The bromide ions were oxidized through the use of an excess of hypochlorite ion, and the signal was generated by reaction with fluorescein. The diminishing fluorescence of a fixed quantity of fluorescein dye upon its reaction with increasing levels of bromine (to a second dye, Eosin Y) is observed in FIG. 6, where the lowest concentration of bromide produced the largest signal (curve 602) and the highest concentration of bromide produced the smallest signal (curve 604).

Figure 7:
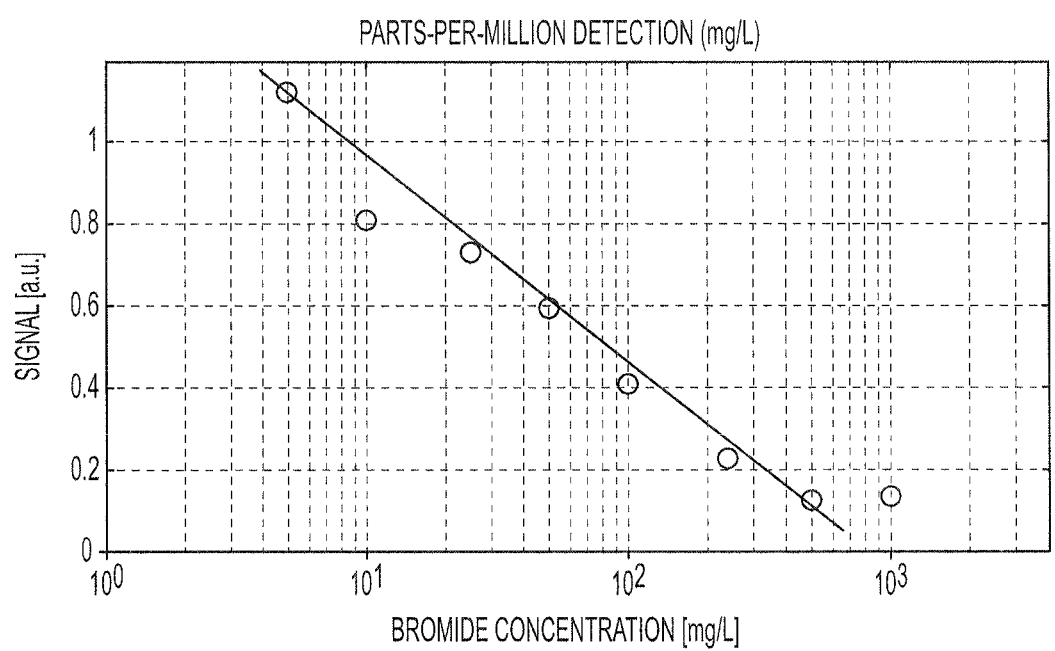
FIG. 7 shows the fluorescence signal of fluorescein dye integrated over 525 to 550 nm versus bromide ion concentrations (mg/L) shown in FIG. 6 obtained using methods in accordance with certain embodiments of the present invention.
Figure 8:
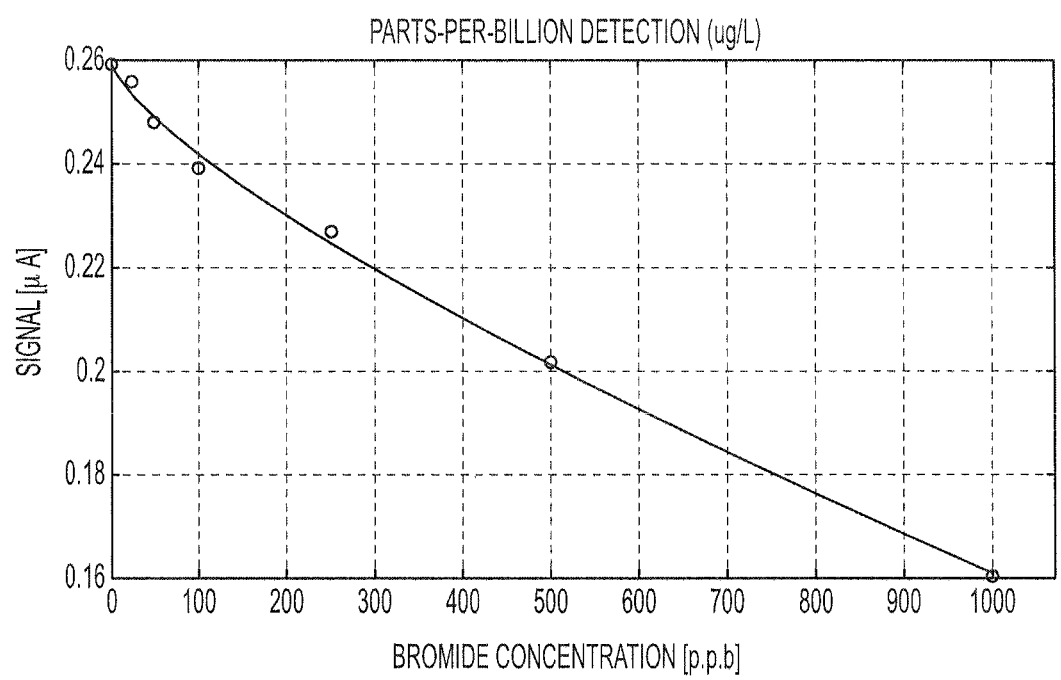
FIG. 8 shows the fluorescence signal of fluorescein dye integrated over 525 to 550 nm versus bromide ion concentration (ug/L) in simulated groundwater obtained using methods in accordance with certain embodiments of the present invention.

FIG. 7 and FIG. 8 each show the fluorescence signal of fluorescein dye versus bromide ion concentration in simulated groundwater analyte (data for FIG. 7 generated using curves shown in FIG. 6). The signal is for 5 to 1,000 mg/L Br—replotted (using an integration of signal from 525 to 550 nm) in the typical Beer's Law log format to show the linearity of response if the data is treated in this manner. The signal is seen to diminish as bromine is produced by the hypochorite ion oxidation of bromide ion and fluorescein reacts with the bromine to produce the dye Eosin Y. Further, the signal is linear over the broad range of bromide ion concentration, from as low as single digit parts-per-billion to as high as several hundred mg/L.

Possible interfering fluorescence, produced by hydroxyl radical oxidation of other constituents that may be found in a groundwater or freshwater sample is unlikely. Total organic carbon (TOC) is present in flow-back water at a median concentration of 63 mg/L, but is unlikely to produce fluorescent species upon oxidation. Its oxidation would only compete for hydroxyl ion, slowing the production of bromine. Iron, present as a hydroxy complex of ferrous ion, is easily oxidized to ferric ion. Manganous ion oxidation to manganese dioxide solids is also likely. Fe and Mn are present in produced water at median concentrations of 39 and 2.6 mg/L respectively. Fe and Mn are present at a combined concentration an order of magnitude below that of the highly reactive bromide ion. Chloride ion is kinetically unlikely to photocatalytically oxidize to either consume hydroxyl radical or produce a soluble species capable of interfering with the bromination of fluorescein to Eosin Y. Experimental work will be necessary to assess the impact of these possible influences on the timeframe required for complete bromide oxidation.

An exemplary dual chamber system may be designed as a submersed flow cell having a first chamber for the photocatalytic oxidation and a second chamber in the form of a rectangular quartz cuvette for the integrated measurement of fluorescence between 525 and 550 nm. Repetitive measurements will be possible using a sampling pump and isolation valves to move successive samples of photocatalytically oxidized water into and out of the measurement cuvette. After analysis, the analyte and remaining fluorescein would then be discharged. Fluorescein and Eosin Y are known to be non-toxic and biodegradable. For example, fluorescein is used by ophthalmologists as a diagnostic stain for the eye, and Eosin Y is a widely used histological stain.

Key elements for an exemplary embodiment of a dual chamber system of the present invention would be a 365 nm UV diode (a commodity item, such as available from LedEngin, inc.), photocatalytic anatase TiO2-coated glass beads (such as available from Cospheric, Inc.) with which to fill the first flow-through UV-transparent chamber, a second similar flow-through quartz cuvette (such as available from Starna, Inc.), in which to do the fluorescein addition and fluorescence measurement, a second UV diode to activate the fluorescein, and a photodetector (such as available from Thorlabs) possibly coupled with a 525 to 550 nm notch filter (such as available from LOT Oriel), and measurement/reporting electronics. Multi-excitation wavelength, filter and photodiode approaches are also possible in embodiments of the present invention.

An exemplary single chamber system may be designed with a single sample chamber in the form of a plastic vessel having at least one UV quality window, such as a quartz window for the integrated measurement of fluorescence between 525 and 550 nm. Repetitive measurements will be possible using a set of injection syringes for pulling sample into the sample chamber and expelling it therefrom, and at least one isolation valves for the reporter compound source. After analysis, the analyte and remaining fluorescein would then be discharged.

While specific embodiments of the invention have been described in detail, it should be appreciated by those skilled in the art that various modifications and alternations and applications could be developed in light of the overall teachings of the disclosure. Furthermore, it is to be understood that these embodiments and implementations are not limited to the particular components, methodologies, or protocols described, as these may vary. The terminology used in the description is for the purpose of illustrating the particular versions or embodiments only, and is not intended to limit their scope in the present disclosure which will be limited only by the appended claims. Accordingly, the particular arrangements, systems, apparatuses, and methods disclosed are meant to be illustrative only and not limiting as to the scope of the invention.

What is claimed is:

1. A single chamber system for detection of bromide ions in an aqueous sample, said system comprising:
    a sample chamber that defines fluid inlet for receiving the aqueous sample, a fluid outlet, and an inner surface, said sample chamber also containing an oxidizing agent for oxidizing bromide ions to form bromine;
    a reporter compound that is luminescent when illuminated by light within a given wavelength band, said reporter compound being of sufficient quantity so that, when mixed with the oxidized water sample in said sample chamber, said reporter compound reacts with bromine in said aqueous sample to produce a mixture of reacted compound that has reacted with said bromine and unreacted reporter compound;
    a reporter light source that illuminates the unreacted reporter compound with light that is within a given band of wavelength;
    an optical detection unit that detects a light emitted by the unreacted reporter compound; and
    a pump to control flow of the aqueous sample into the sample chamber and flow of the mixture of reacted compound and unreacted reporter compound out of the sample chamber.

2. The single chamber system of claim 1 wherein said sample chamber includes a photocatalyst that produces said oxidizing agent when illuminated by light within a given frequency in the presence of water, said photocatalyst producing hydroxyl radicals; and an oxidizing light source that illuminates said photocatalyst to produce hydroxyl radicals.

3. The single chamber system of claim 2, wherein at least a first portion of the sample chamber is capable of passing a light signal from the oxidizing light source, and at least a second portion of the detection chamber is capable of passing the light signal from the reporter light source.

4. The single chamber system of claim 2, wherein the oxidizing and reporter light sources are LEDs.

5. The single chamber system of claim 1, wherein the optical detection unit is a photodiode, a photodiode array, a charge coupled device, or a photomultiplier tube.

6. The single chamber system of claim 1, further comprising:
    a wavelength filter placed in front of the optical detection unit, wherein the wavelength filter limits the signal from the reporter light source to light corresponding to the characteristic emission of the reporter compound.

7. The single chamber system of claim 1, further comprising:
    a probe attachable to the fluid inlet of the sample chamber, wherein the aqueous sample flows into and through the probe into the fluid inlet of the sample chamber.

8. The single chamber system of claim 1, further comprising:
    a first injection syringe configured to inject a buffer solution to the aqueous sample in the sample chamber; and
    a second injection pump and motor configured to inject the reporter compound into the sample chamber.

9. The single chamber system of claim 8, further comprising:
    programmable electronic computing means for controlling the sequencing of the injection syringes, the oxidizing and reporter light sources, the optical detection unit and the pump.

10. The single chamber system of claim 1, wherein the photocatalyst is provided as a coating on the inner surface of the sample chamber or as a coating on glass beads contained within the sample chamber.

11. The single chamber system of claim 1, wherein the reporter compound is a chemical dye selected from the group comprising fluorescein, phenol red, methyl orange, brom cresol purple, phenosafranin, rosaniline, and N,N-Diethyl-p-Phenylenediamine Oxalate.

12. The single chamber system of claim 1, wherein the reporter compound is fluorescein.

13. A dual chamber system for detection of bromide ions in an aqueous sample, comprising:
a reaction chamber having a fluid inlet for receiving the aqueous sample, a fluid outlet, and an inner surface;
a photocatalyst that is included in the reaction chamber;
a detection chamber having a fluid inlet and a fluid outlet, wherein the detection chamber is configured to receive fluid from the fluid outlet of the reaction chamber;
an oxidizing light source configured to illuminate at least a portion of the reaction chamber to cause the photocatalyst, in the presence of water, to generate an oxidizing agent that converts the bromide ions is said aqueous sample to bromine;
a reporter compound source that is in fluid communication with the fluid outlet of the reaction chamber, said reporter compound being of sufficient quantity to react with the bromine in said aqueous sample to form a mixture of reacted reporter compound and unreacted reporter compound;
a reporter light source configured to illuminate at least a portion of the detection chamber to cause the unreacted reporter compound to luminesce; and
an optical detection unit capable of receiving a light signal that is emitted from the unreacted reporter compound so as to measure the concentration of bromine in accordance with the light signal from the unreacted reporter compound.

14. The dual chamber system of claim 13, wherein at least a portion of the reaction chamber is capable of passing a light signal from the oxidizing light source, and at least a portion of the detection chamber is capable of passing a light signal from the reporter light source.

15. The dual chamber system of claim 13, further comprising:
an injection valve at the fluid inlet of the reaction chamber;
a valve at the fluid outlet of the reporter compound source;
a valve at the fluid outlet of the detection chamber; and
a pump configured to move the fluid sample from the fluid inlet of the reaction chamber to a fluid outlet of the detection chamber.

16. The dual chamber system of claim 15, further comprising:
programmable electronic computing means for controlling the sequencing of the valves and the pump.

17. The dual chamber system of claim 13, wherein the photocatalyst comprises a coating on the inner surface of the reaction chamber, or a coating on glass beads contained within the reaction chamber.

18. A method for detection of bromide ions in an aqueous sample, comprising:
providing a volume of aqueous sample;
admixing the volume of aqueous sample with a photocatalyst;
exposing the volume of aqueous sample admixed with the photocatalyst to a source of light to produce free hydroxyl radicals that react with bromide ions in the aqueous sample to produce bromine; and
admixing a reporter compound with the volume of aqueous sample containing bromine, wherein the reporter compound is of sufficient quantity that, when mixed with the aqueous sample containing bromine, the bromine reacts with the reporter compound to produce a mixture of reacted compound and unreacted reporter compound;
illuminating the unreacted reporter compound with light that is which a given band of wavelength to cause the unreacted reporter compound to luminesce; and
detecting, light emitted by the luminescent unreacted reporter compound to determine the concentration of bromine.

19. The method of claim 18, wherein the photocatalyst is anatase $TiO_2$.

20. The method of claim 18, wherein the reporter compound is a chemical dye selected from the group comprising fluorescein, phenol red, methyl orange, brom cresol purple, phenosafranin, and N,N-Diethyl-p-Phenylenediamine Oxalate.

21. The method of claim 18, wherein the reporter compound is fluorescein.

* * * * *